(12) United States Patent
Jamison et al.

(10) Patent No.: US 11,768,138 B2
(45) Date of Patent: Sep. 26, 2023

(54) METHODS TO USE CHEMO-RESISTIVE SENSORS FOR WELLBORE PRODUCTION

(71) Applicant: Halliburton Energy Services, Inc., Houston, TX (US)

(72) Inventors: Dale E. Jamison, Humble, TX (US); William W. Shumway, Spring, TX (US); Preston A. May, Montgomery, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 224 days.

(21) Appl. No.: 17/219,114

(22) Filed: Mar. 31, 2021

(65) Prior Publication Data

US 2022/0317001 A1 Oct. 6, 2022

(51) Int. Cl.
| | |
|---|---|
| *G01N 1/44* | (2006.01) |
| *G01N 1/20* | (2006.01) |
| *G01N 33/28* | (2006.01) |
| *G01N 27/12* | (2006.01) |
| *G01N 33/00* | (2006.01) |

(52) U.S. Cl.
CPC ............. *G01N 1/44* (2013.01); *G01N 1/2035* (2013.01); *G01N 27/12* (2013.01); *G01N 33/0016* (2013.01); *G01N 33/2823* (2013.01); *G01N 2001/205* (2013.01)

(58) Field of Classification Search
CPC ........ G01N 1/44; G01N 1/2035; G01N 27/12; G01N 33/0016; G01N 33/2823; G01N 2001/205
See application file for complete search history.

(56) References Cited

U.S. PATENT DOCUMENTS

| | | | | |
|---|---|---|---|---|
| 1,376,631 | A | * | 5/1921 | Newton .................. C10G 7/00 202/185.1 |
| 2,229,884 | A | * | 1/1941 | Chalkley ............... E21B 49/005 73/19.09 |
| 2,591,737 | A | * | 4/1952 | Souther, Jr. ........... E21B 49/005 250/301 |

(Continued)

OTHER PUBLICATIONS

Lin et al. "Preoxidation for Colorimetric Sensor Array Detection of VOCs," Journal of the American Chemical Society, 133(42), pp. 16786-16789 (Year: 2011).*

(Continued)

*Primary Examiner* — John Fitzgerald
(74) *Attorney, Agent, or Firm* — Thomas Rooney; C. Tumey Law Group PLLC

(57) ABSTRACT

The disclosure provides a method for determining a composition of a fluid. The method comprises diverting a sample of a portion of the fluid to a test chamber. The method further comprises actuating a heat source disposed around the test chamber to increase the temperature within the test chamber to produce vapors from the sample of the portion of the fluid and directing the vapors from the sample of the portion of the fluid to a chemical sensor array comprising one or more chemical sensors. The method further comprises determining a composition of the vapors from the sample of portion of the fluid, wherein the composition of the vapors is associated with the composition of the fluid.

15 Claims, 4 Drawing Sheets

(56) References Cited

U.S. PATENT DOCUMENTS

| | | | | |
|---|---|---|---|---|
| 2,608,866 | A * | 9/1952 | Breedlove | G01N 1/2035 73/863.61 |
| 3,429,186 | A * | 2/1969 | Price | G01N 1/22 73/863.61 |
| 4,307,620 | A * | 12/1981 | Jiskoot | G01N 1/2035 73/863.61 |
| 4,416,152 | A * | 11/1983 | Wilson | E21B 49/10 166/100 |
| 4,434,653 | A * | 3/1984 | Montgomery | E21B 49/10 166/100 |
| 4,507,957 | A * | 4/1985 | Montgomery | E21B 49/10 166/100 |
| 4,724,008 | A * | 2/1988 | Bell | G01N 27/12 134/2 |
| 5,115,687 | A * | 5/1992 | Clingman, Jr. | G01N 33/225 73/863.61 |
| 6,443,001 | B1 * | 9/2002 | Duriez | E21B 21/06 73/19.01 |
| 7,003,405 | B1 * | 2/2006 | Ho | G01V 9/007 702/9 |
| 7,159,445 | B2 | 1/2007 | Bohm et al. | |
| 7,243,536 | B2 * | 7/2007 | Bolze | E21B 49/081 166/264 |
| 7,395,704 | B2 | 7/2008 | DiFoggio | |
| 7,741,605 | B2 * | 6/2010 | Gunn | E21B 21/01 250/269.1 |
| 8,997,562 | B2 * | 4/2015 | Schexnaider | F28D 7/0008 73/152.19 |
| 10,018,613 | B2 | 7/2018 | Potyrailo et al. | |
| 10,025,000 | B2 | 7/2018 | Monteiro et al. | |
| 2003/0033866 | A1 * | 2/2003 | Diakonov | E21B 49/081 73/152.55 |
| 2004/0069046 | A1 * | 4/2004 | Sunshine | G01N 33/0009 422/90 |
| 2004/0159149 | A1 | 8/2004 | Williams et al. | |
| 2012/0137764 | A1 | 6/2012 | Lawrence et al. | |
| 2012/0178653 | A1 | 7/2012 | McClung, III | |
| 2013/0269411 | A1 | 10/2013 | Selman et al. | |
| 2013/0319104 | A1 * | 12/2013 | Schexnaider | G01N 33/241 73/152.42 |
| 2014/0202664 | A1 * | 7/2014 | Schexnaider | F28F 21/083 165/104.19 |
| 2014/0298899 | A1 * | 10/2014 | Schexnaider | G01N 33/2823 165/61 |
| 2016/0238547 | A1 | 8/2016 | Park et al. | |
| 2016/0273355 | A1 * | 9/2016 | Gosney | E21B 21/01 |
| 2017/0115263 | A1 | 4/2017 | Monteiro | |
| 2019/0383720 | A1 * | 12/2019 | Savoy | G01N 33/18 |
| 2020/0400629 | A1 * | 12/2020 | Mulzer | G01N 27/12 |

OTHER PUBLICATIONS

International Search Report and Written Opinion for PCT/US2021/025447 dated Nov. 17, 2022.

Lin H., et al., "Preoxidation for Colorimetric Sensor Array Detection of VOCs," Journal of the American Cancer Society, 2011, pp. 16786-16789, V. 133(42), ACS Publications.

Garcia-Hernandez, A., et al., "Leak Detectability in an Off-shore Multiphase Production System," Pipeline Simulation Interest Group (PSIG) Annual Meeting, Vancouver, British Columbia, May 2016.

Bylin, C., et al., "Designing the Ideal Offshore Platform Methane Mitigation Strategy," Society of Petroleum Engineers (SPE), Jan. 2010, SPE International Conference on Health, Safety and Environment in Oil and Gas Exploration and Production, SPE126964-MS.

Stundner, M., et al., "Production Performance Monitoring Workflow," Society of Petroleum Engineers (SPE), Jan. 2006, First International Oil Conference and Exhibition, SPE103757-MS.

Hooimeijer, M., et al., "Advanced Production Monitoring," Society of Petroleum Engineers (SPE), Jan. 2006, SPE International Oil & Gas Conference and Exhibition, SPE104161-MS.

Abdallah, D., et al., "Asphaltene Studies in On-Shore Abu Dhabi Fields, Part IV: Development of a Surface Sensor," Society of Petroleum Engineers(SPE), Sep. 2018, SPE Annual Technical Conference and Exhibition, SPE191676-MS.

International Search Report and Written Opinion issued in related PCT Application No. PCT/US2021/025447 dated Dec. 23, 2021, 10 pages.

* cited by examiner

METHODS TO USE CHEMO-RESISTIVE SENSORS FOR WELLBORE PRODUCTION

TECHNICAL FIELD OF THE INVENTION

The present disclosure relates generally to chemical sensors in fluid operations and, more particularly, to systems and methods for determining a composition of a fluid.

BACKGROUND

During the drilling and completion of oil and gas wells, it may be necessary to engage in ancillary operations, such as evaluating the production capabilities of formations intersected by the wellbore. For example, after a well or well interval has been drilled, zones of interest are often tested or sampled to determine various formation properties such as permeability, fluid type, fluid quality, formation temperature, formation pressure, bubblepoint and formation pressure gradient. The acquisition of accurate data from the wellbore is critical to the optimization of hydrocarbon wells. This wellbore data can be used to determine the location and quality of hydrocarbon reserves, whether the reserves can be produced through the wellbore, and for well control during drilling operations.

Figure 1:
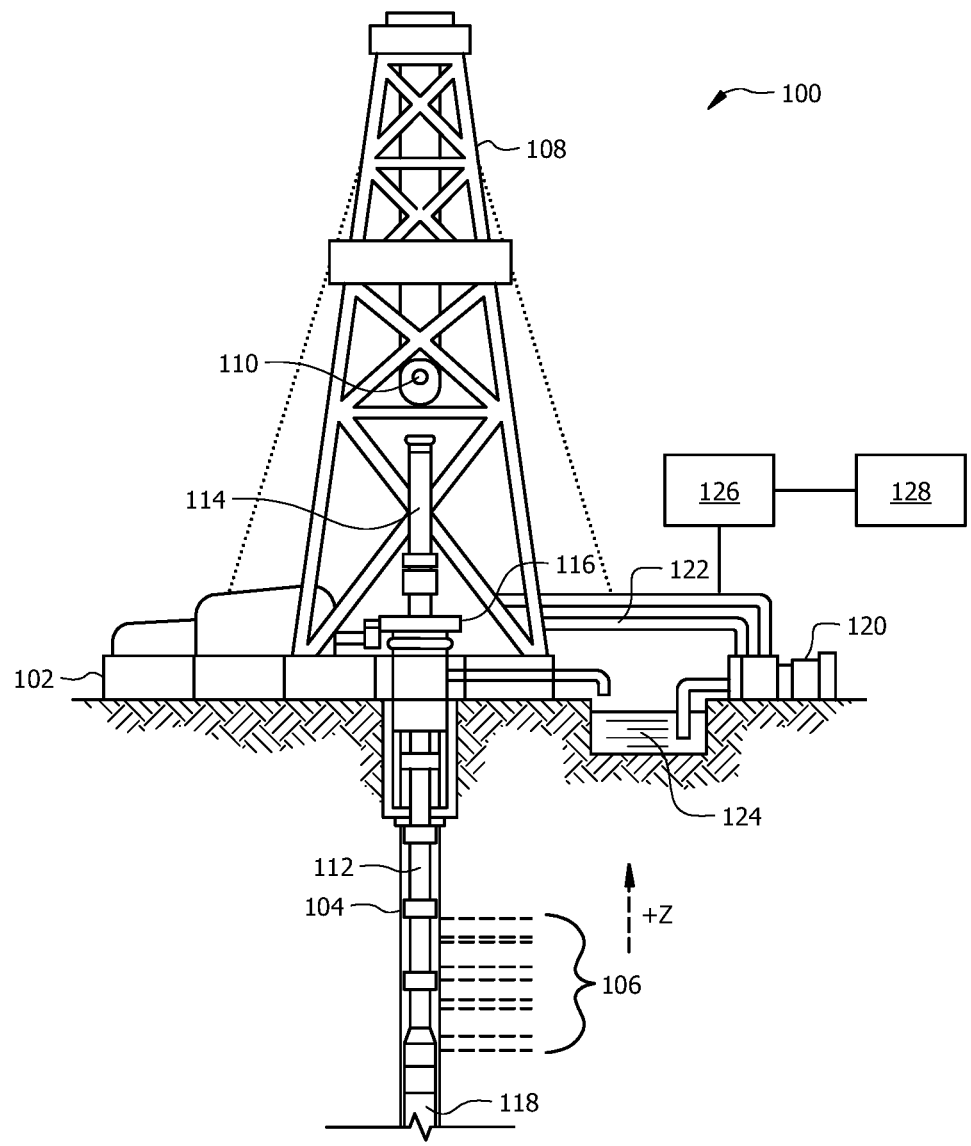
FIG. 1 is a schematic diagram of a drilling system at a well site, according to one or more aspects of the present disclosure.

While embodiments of this disclosure have been depicted and described and are defined by reference to exemplary embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DETAILED DESCRIPTION

Illustrative embodiments of the present invention are described in detail herein. In the interest of clarity, not all features of an actual implementation may be described in this specification. It will of course be appreciated that in the development of any such actual embodiment, numerous implementation-specific decisions may be made to achieve the specific implementation goals, which may vary from one implementation to another. Moreover, it will be appreciated that such a development effort might be complex and time consuming but would nevertheless be a routine undertaking for those of ordinary skill in the art having the benefit of the present disclosure.

Throughout this disclosure, a reference numeral followed by an alphabetical character refers to a specific instance of an element and the reference numeral alone refers to the element generically or collectively. Thus, as an example (not shown in the drawings), widget "1a" refers to an instance of a widget class, which may be referred to collectively as widgets "1" and any one of which may be referred to generically as a widget "1". In the figures and the description, like numerals are intended to represent like elements.

To facilitate a better understanding of the present disclosure, the following examples of certain embodiments are given. In no way should the following examples be read to limit, or define, the scope of the disclosure. Embodiments described below with respect to one implementation are not intended to be limiting.

For purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a personal computer, a network storage device, or any other suitable device and may vary in size, shape, performance, functionality, and price. The information handling system may include random access memory (RAM), one or more processing resources such as a central processing unit (CPU) or hardware or software control logic, ROM, and/or other types of nonvolatile memory. Additional components of the information handling system may include one or more disk drives, one or more network ports for communication with external devices as well as various input and output (I/O) devices, such as a keyboard, a mouse, and a video display. The information handling system may also include one or more buses operable to transmit communications between the various hardware components. The information handling system may also include one or more interface units capable of transmitting one or more signals to a controller, actuator, or like device.

For the purposes of this disclosure, computer-readable media may include any instrumentality or aggregation of instrumentalities that may retain data and/or instructions for a period of time. Computer-readable media may include, for example, without limitation, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory (EEPROM), and/or flash memory; as well as communications media such wires, optical fibers, microwaves, radio waves, and other electromagnetic and/or optical carriers; and/or any combination of the foregoing.

The terms "couple" or "couples," as used herein, are intended to mean either an indirect or direct connection. Thus, if a first device couples to a second device, that connection may be through a direct connection, or through an indirect electrical connection or a shaft coupling via other devices and connections.

The present disclosure provides for systems and methods for determining a composition of a fluid from a well site. The provided systems and methods may be able provide analysis of vapors produced from the fluid to determine the different components and percent quantity of each. In one or more embodiments, a chemical sensor system may comprise one or more electro-chemical resistor sensors configured to collectively determine a plurality of potential compositions.

FIG. 1 is a schematic diagram of an exemplary drilling system 100 that may employ the principles of the present disclosure, according to one or more embodiments. As illustrated, the drilling system 100 may include a drilling platform 102 positioned at the surface and a wellbore 104 that extends from the drilling platform 102 into one or more subterranean formations 106. In other embodiments, such as in an offshore drilling operation, a volume of water may separate the drilling platform 102 and the wellbore 104. Even though FIG. 1 depicts a land-based drilling platform 102, it will be appreciated that the embodiments of the present disclosure are equally well suited for use in other types of drilling platforms, such as offshore platforms, or rigs used in any other geographical locations. The present disclosure contemplates that wellbore 104 may be vertical, horizontal or at any deviation.

The drilling system 100 may include a derrick 108 supported by the drilling platform 102 and having a traveling block 110 for raising and lowering a conveyance 112, such as a drill string. A kelly 114 may support the conveyance 112 as it is lowered through a rotary table 116. A drill bit 118 may be coupled to the conveyance 112 and driven by a downhole motor and/or by rotation of the conveyance 112 by the rotary table 116. As the drill bit 118 rotates, it creates the wellbore 104, which penetrates the subterranean formations 106. A pump 120 may circulate drilling fluid through a feed pipe 122 and the kelly 114, downhole through the interior of conveyance 112, through orifices in the drill bit 118, back to the surface via the annulus defined around conveyance 112, and into a retention pit 124. The drilling fluid cools the drill bit 118 during operation and transports cuttings from the wellbore 104 into the retention pit 124.

The drilling system 100 may further include a bottom hole assembly (BHA) coupled to the conveyance 112 near the drill bit 118. The BHA may comprise various downhole measurement tools such as, but not limited to, measurement-while-drilling (MWD) and logging-while-drilling (LWD) tools, which may be configured to take downhole measurements of drilling conditions. The MWD and LWD tools may include at least one acoustic logging device, which may comprise one or more transmitters capable of transmitting one or more acoustic signals into the surrounding one or more subterranean formations 106.

As the drill bit 118 extends the wellbore 104 through the formations 106, the acoustic logging device may continuously or intermittently transmit signals and receive back signals relating to a parameter of the formations 106. The acoustic logging device and other sensors of the MWD and LWD tools may be communicably coupled to a telemetry module used to transfer measurements and signals from the BHA to a surface receiver (not shown) and/or to receive commands from the surface receiver. The telemetry module may encompass any known means of downhole communication including, but not limited to, a mud pulse telemetry system, an acoustic telemetry system, a wired communications system, a wireless communications system, or any combination thereof. In certain embodiments, some or all of the measurements taken at the acoustic logging device may also be stored within the acoustic logging device or the telemetry module for later retrieval at the surface upon retracting the conveyance 112.

The drilling system 100 may further include a chemical sensor system 126 disposed about the drilling platform 102. The chemical sensor system 126 may be operable to determine the composition of a sample of a fluid. In one or more embodiments, the chemical sensor system 126 may be incorporated into the drilling system 100 in any suitable manner. For example, the chemical sensor system 126 may be disposed about one or more conduits and operable to direct a portion of a flow of a fluid to be analyzed by the chemical sensor system 126. The chemical sensor system 126 may be communicatively coupled to an information handling system 128 for processing information obtained by the chemical sensor system 126. The drilling system 100 may include an information handling system 128 for controlling, processing, storing, and/or visualizing the measurements gathered by the chemical sensor system 126. The information handling system 128 may be communicably coupled to the chemical sensor system 126 by way any suitable wired or wireless connection. In one or more embodiments, the information handling system 128 may be disposed about any suitable location in the drilling system 100. In alternate embodiments, information handling system 128 may be located remotely from the system 100. The information handling system 128 may be directly or indirectly coupled to any one or more components of the drilling system 100.

Figure 2:
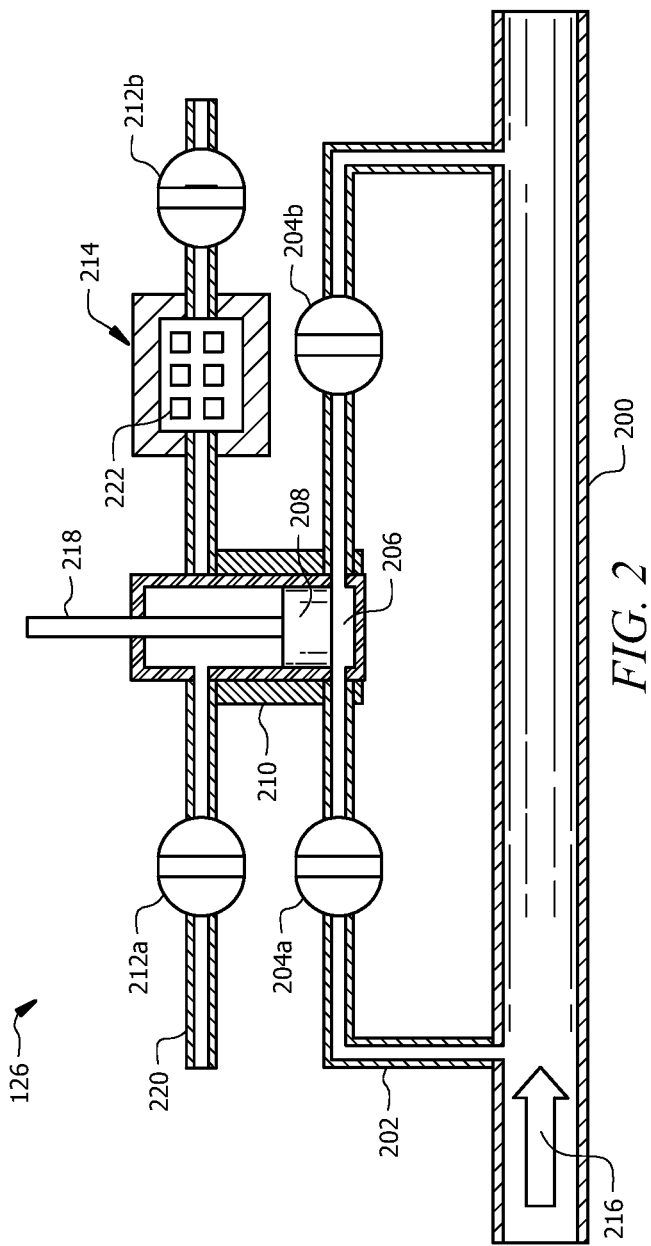
FIG. 2 is a diagram illustrating an example chemical sensor system, according to aspects of the present disclosure.

FIG. 2 illustrates an example chemical sensor system 126 incorporated into a main conduit 200 of the drilling system 100 (referring to FIG. 1). As illustrated, the chemical sensor system 126 may comprise a diverting conduit 202, a first set of valves 204a and 204b, a test chamber 206, a piston 208, a heat source 210, a second set of valves 212a and 212b, and a chemical sensor array 214. The main conduit 200 and the diverting conduit 202 may comprise any suitable size, height, shape, and any combinations thereof. Further, the main conduit 200 and the diverting conduit 202 may comprise any suitable materials, such as metals, nonmetals, polymers, composites, and any combinations thereof. In embodiments, the main conduit 200 may be a conduit or piping operable to direct a return flow of a fluid 216 from the wellbore 104 (referring to FIG. 1) to equipment downstream for processing and/or recovery. The diverting conduit 202 may be a separate conduit or piping disposed in parallel to the flow of fluid 216 with the main conduit 200. While main conduit 200 may be configured to direct a return flow of the fluid 216, diverting conduit 202 may be operable to divert a portion of the flow of fluid 216 from the main conduit 200 for processing by the chemical sensor system 126.

The first set of valves 204a and 204b may be disposed along the diverting conduit 202. In embodiments, any suitable valve may be used as each of the first set of valves 204a and 204b. The first set of valves 204a and 204b may be configured to open and close to allow for the portion of the flow of fluid 216 to be diverted from the main conduit 200 along the diverting conduit 202. When the first set of valves 204a and 204b is in an open position, the portion of the flow of fluid 216 may be able to flow through the diverting conduit 202. When the first set of valves 204a and 204b is in a closed position, the portion of the flow of fluid 216 may be inhibited from flowing past each of valves 204a,b along the diverting conduit 202. In embodiments, each of the first set of valves 204a and 204b may be configured to actuate separately from each other.

As illustrated, the test chamber 206 may be disposed between the first set of valves 204a and 204b. The test chamber 206 may be configured to receive and contain a sample of the portion of the flow of fluid 216. The test chamber 206 may comprise any suitable size, height, shape, and any combinations thereof. Further, the test chamber 206 may comprise any suitable materials, such as metals, nonmetals, polymers, composites, and any combinations thereof. As shown in FIG. 2, the piston 208 may be disposed within the test chamber 206. The piston 208 may be configured to translated within the test chamber 206. A rod 218 coupled to the piston 208 may be used to actuate the piston 208 for translation within the test chamber 206. The rod 218 may be coupled to any external component capable of operating the piston 208. Further and without limitations, there may be a secondary conduit 220 disposed parallel to and vertically above the diverting conduit 202, wherein the test chamber 206 is fluidly coupled to the secondary conduit 220. While the secondary conduit 220 is illustrated as being parallel to the diverting conduit 202, the disclosure is not limited to such a configuration. As illustrated, the second set of valves 212a and 212b may be disposed along the secondary conduit 220 on opposite sides of the test chamber 206.

In embodiments, any suitable valve may be used as each of the second set of valves 212a and 212b. The second set of valves 212a and 212b may be configured to open and close to allow for any suitable fluid (for example, a liquid, gas, or combination thereof) to flow through the secondary conduit 220. In one or more embodiments, each of the second set of valves 212a and 212b may be configured to actuate separately from each other and may be actuated based, at least in part, on operation of the piston 208.

In embodiments, the piston 208 may be disposed fully extended in a first position. In the first position, the piston 208 may be disposed vertically below a central axis of the secondary conduit 220. The sample of the portion of the flow of fluid 216 may flow into the test chamber 206 while the piston 208 is at the first position. During operations, the first set of valves 204a,b may be actuated to close once the test chamber 206 receives the sample of the portion of the flow of fluid 216. In embodiments, the second set of valves 212a and 212b may be in a closed position while the piston 208 is in the first position. The valve 212b may be actuated to an open position to allow for movement of the piston 208 to a second position. In response, the piston 208 may be actuated to translate within the test chamber 206 to the second position. As the piston 208 translates to the second position, the piston 208 may cross the central axis of the secondary conduit 220, within the test chamber 206, and come to abut the top of the test chamber 206 above the central axis of the secondary conduit 220.

Once the piston 208 is in the second position, the heat source 210 may be actuated to increase the temperature within the test chamber 206. As shown, the heat source 210 is disposed around the test chamber 206. Any suitable configuration between the heat source 210 and the test chamber 206 capable of allowing the heat source 210 to increase the temperature within the test chamber 206 is contemplated herein. The heat source 210 may comprise any suitable size, height, shape, and any combinations thereof. Further, any suitable heater or component functionally capable of providing heat may be used as the heat source 210. During operations, the heat source 210 may be configured to increase the temperature within the test chamber to produce vapors from the sample of the portion of the flow of fluid 216. The production of vapors from the flow of fluid 216 may produce volatile organic compounds (VOCs), wherein analysis of VOCs may be more efficient and/or than analyzing the fluid 216. As the valve 212b is in the open position and valve 212a remains in the closed position, the vapors from the sample of the portion of the flow of fluid 216 may flow out of the test chamber 206 and through the secondary conduit 220.

The vapors from the sample of the portion of the flow of fluid 216 may flow to the chemical sensor array 214 as it flows through the secondary conduit 220. The chemical sensor array 214 may be disposed along the secondary conduit 220, as seen in FIG. 2. In one or more embodiments, the chemical sensor array 214 may be disposed about any suitable location within the chemical sensor system 126. The chemical sensor array 214 may comprise any suitable size, height, shape, and any combinations thereof. Further, the chemical sensor array 214 may comprise any suitable materials, such as metals, nonmetals, polymers, composites, and any combinations thereof. The chemical sensor array 214 may be configured to house one or more chemical sensors 222 operable to determine a composition of the vapors from the sample of the portion of the flow of fluid 216. In one or more embodiments, the one or more chemical sensors 222 may be disposed and configured in any suitable manner in relation to the chemical sensor array 214. The chemical sensor array 214 may be communicatively coupled to the information handling system 128 (referring to FIG.) and may be configured to transmit data, measurement, information, and the like to the information handling system 128 for further processing. In one or more embodiments, the fluid 216 may be pre-treated prior to analysis by the chemical sensor array 214. For example, there may be production of VOCs from the portion of the flow of fluid 216, as disclosed. Without limitations, any suitable pre-treatment of the fluid 216 may be applicable, including oxidation, reduction, applying acids and/or bases, electrochemistry, thermal energy, microwave energy, ultraviolet irradiation, or any combinations thereof. The chemical sensor array 214 may be operable to determine composition of VOCs and the quantity of VOCs, resin concentration, asphaltene concentration, inferred oil viscosity, inferred oil surface tension, enhanced reservoir modeling, optimization of production, and any combinations thereof.

In embodiments, the vapors from the sample of the portion of the flow of fluid 216 may be inhibited by valve 212b from continuing to flow as the chemical sensor array 214 operates. Once the chemical sensor array 214 has finished operating, a purging cycle may begin throughout the chemical sensor system 126. Valve 212b may be actuated from a closed position to an open position, thereby allowing the vapors from the sample of the portion of the flow of fluid 216 to flow out of the chemical sensor array 214 and further downstream. Further, valve 204b may be actuated to an open position to allow for pressure equalization for movement of the piston 208. The piston 208 may be actuated to translate from the second position to the first position. Once the piston 208 translates past the central axis of the secondary conduit 220, the valve 212a may be actuated to an open position, wherein the valve 212a is disposed upstream of the test chamber 206. A flow of a secondary fluid (not shown) may be introduced through the secondary conduit 220, into and through the test chamber 206, through the chemical sensor array 214, and out through valve 212b. The secondary fluid may be any suitable fluid capable of cleaning the aforementioned components. The second set of valves 212a,b may be actuated to the closed position once the secondary fluid has cleaned the components. Then, valve 204a may be actuated to an open position to allow any remaining sample of the portion of the flow of fluid 216 and vapors from the sample to flow out of the test chamber and/or diverting conduit 202. The chemical sensor system 126 may then repeat the aforementioned process to analyze a portion of the flow of fluid 216 to determine the composition of the fluid 216 any suitable number of times and for any suitable period of time.

Figure 3:
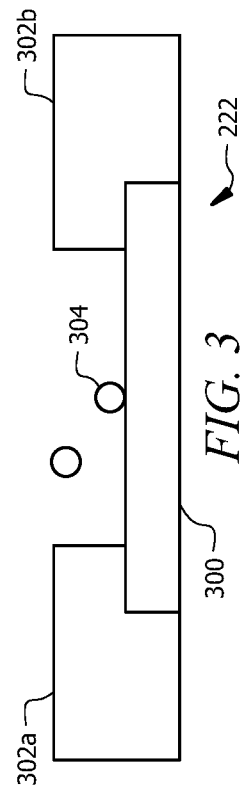
FIG. 3 is a diagram illustrating an example chemical sensor, according to aspects of the present disclosure.

FIG. 3 illustrates an example one of the one or more chemical sensors 222. As illustrated, the chemical sensor 222. The chemical sensor 222 may be any suitable chemiresistor operable to changes its electrical resistance in response to changes in the nearby chemical environment. The chemical sensor 222 may comprise of a sensing material 300 disposed between a set of electrodes 302a and 302b. The resistance between the set of electrodes 302a and 302b may be measurable by any suitable computing device. The sensing material 300 may have an inherent resistance that can be modulated by the presence or absence of a gas particle 304. During exposure, one or more gas particles 304 may interact with the sensing material 300. These interactions may cause changes in the resistance measurement. In embodiments, the resistance changes may simply indicate the presence of one or more gas particles 304. In others, the resistance changes may be proportional to the amount of the one or more gas particles 304 present, allowing for the amount of each gas particle 304 to be measured. For example, one of the one of the one or more chemical sensors 222 may be configured to analyze a specific type of compound, such as paraffins or naphthalenes, and another one of the one or more chemical sensors 222 may be configured to analyze a different type of compound, such as aromatics. In embodiments, each one of the one or more chemical sensors 222 disposed within the chemical sensor array 214 (referring to FIG. 2) may be configured to measure at least one individual type of compound, wherein collectively, the chemical sensor array 214 may be operable to determine a plurality of compositions within the vapors from the sample of the portion of the flow of fluid 216 (referring to FIG. 2).

Figure 4:
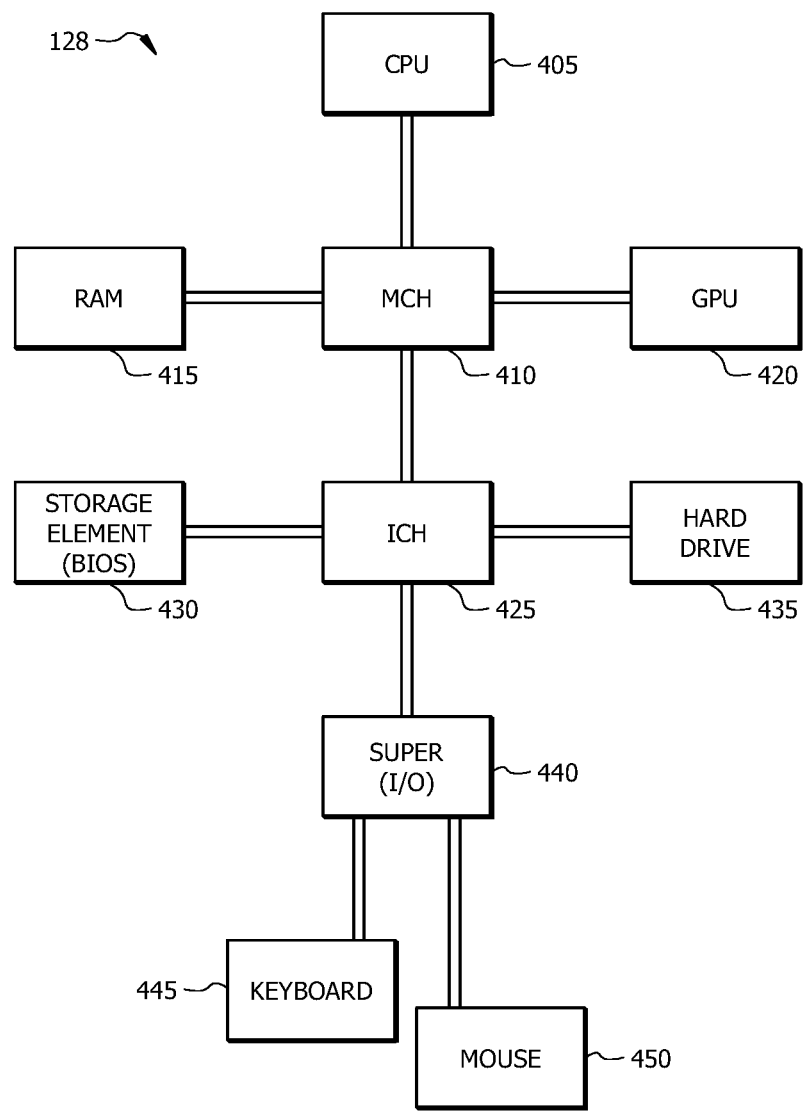
FIG. 4 is a diagram illustrating an example information handling system, according to aspects of the present disclosure.

FIG. 4 is a diagram illustrating an example information handling system 128, according to aspects of the present disclosure. A processor or central processing unit (CPU) 405 of the information handling system 128 is communicatively coupled to a memory controller hub or north bridge 410. The processor 405 may include, for example a microprocessor, microcontroller, digital signal processor (DSP), application specific integrated circuit (ASIC), or any other digital or analog circuitry configured to interpret and/or execute program instructions and/or process data. Processor 405 may be configured to interpret and/or execute program instructions or other data retrieved and stored in any memory such as memory 415 or hard drive 435. Program instructions or other data may constitute portions of a software or application for carrying out one or more methods described herein. Memory 415 may include read-only memory (ROM), random access memory (RAM), solid state memory, or disk-based memory. Each memory module may include any system, device or apparatus configured to retain program instructions and/or data for a period of time (e.g., computer-readable non-transitory media). For example, instructions from a software or application may be retrieved and stored in memory 415 for execution by processor 405.

Modifications, additions, or omissions may be made to FIG. 4 without departing from the scope of the present disclosure. For example, FIG. 4 shows a particular configuration of components of information handling system 128. However, any suitable configurations of components may be used. For example, components of information handling system 128 may be implemented either as physical or logical components. Furthermore, in some embodiments, functionality associated with components of information handling system 128 may be implemented in special purpose circuits or components. In other embodiments, functionality associated with components of information handling system 128 may be implemented in configurable general-purpose circuit or components. For example, components of information handling system 128 may be implemented by configured computer program instructions.

Memory controller hub (MCH) 410 may include a memory controller for directing information to or from various system memory components within the information handling system 128, such as memory 415, storage element 430, and hard drive 435. The memory controller hub 410 may be coupled to memory 415 and a graphics processing unit (GPU) 420. Memory controller hub 410 may also be coupled to an I/O controller hub (ICH) or south bridge 425. I/O controller hub 425 is coupled to storage elements of the information handling system 128, including a storage element 430, which may comprise a flash ROM that includes a basic input/output system (BIOS) of the computer system. I/O controller hub 425 is also coupled to the hard drive 435 of the information handling system 128. I/O controller hub 425 may also be coupled to a Super I/O chip 440, which is itself coupled to several of the I/O ports of the computer system, including keyboard 445 and mouse 450.

In certain embodiments, the information handling system 128 may comprise at least a processor and a memory device coupled to the processor that contains a set of instructions that when executed cause the processor to perform certain actions. In any embodiment, the information handling system 128 may include a non-transitory computer readable medium that stores one or more instructions where the one or more instructions when executed cause the processor to perform certain actions. As used herein, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a computer terminal, a network storage device, or any other suitable device and may vary in size, shape, performance, functionality, and price. The information handling system 128 may include random access memory (RAM), one or more processing resources such as a central processing unit (CPU) or hardware or software control logic, read only memory (ROM), and/or other types of nonvolatile memory. Additional components of the information handling system 128 may include one or more disk drives, one or more network ports for communication with external devices as well as various input and output (I/O) devices, such as a keyboard, a mouse, and a video display. The information handling system 128 may also include one or more buses operable to transmit communications between the various hardware components.

Figure 5:
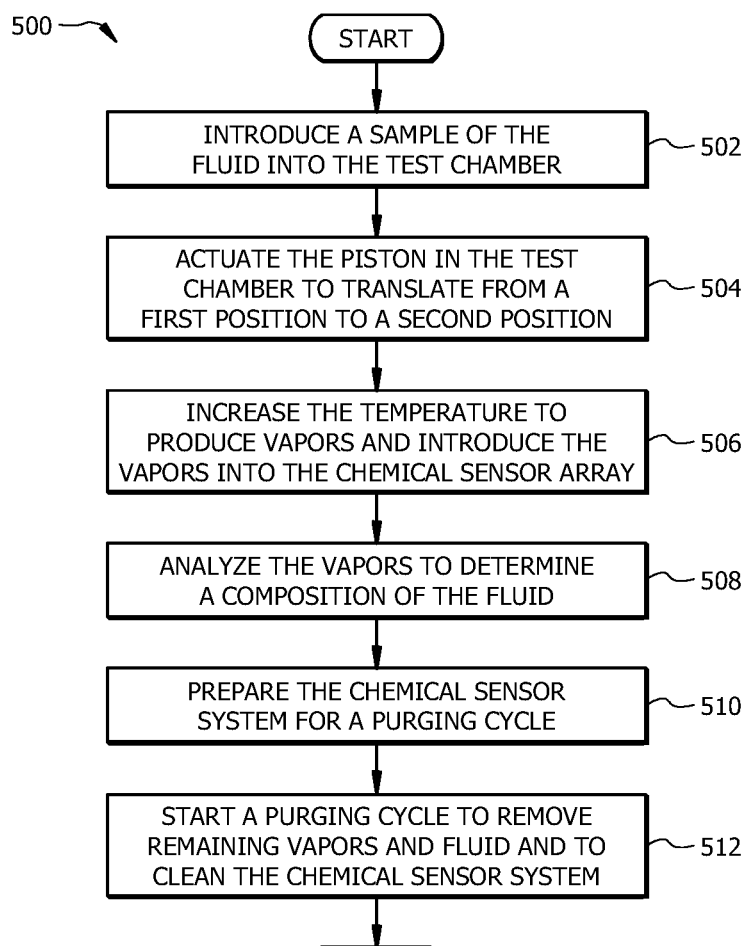
FIG. 5 is a diagram illustrating an example method of operation of the chemical sensor system of FIG. 2, according to aspects of the present disclosure.

FIG. 5 is a flow diagram illustrating an example method 500 of the chemical sensor system 126 of FIG. 1. The method 500 may begin at step 502 where a portion of the flow of fluid 216 (referring to FIG. 2) may be diverted to the test chamber 206 (referring to FIG. 2) through the diverting conduit 202 (referring to FIG. 2). The test chamber 206 may be disposed between the first set of valves 204a,b (referring to FIG. 2), wherein both are initially in a closed position. The first set of valves 204a,b are then actuated to an open position so that a sample of the portion of the flow of fluid 216 may enter into the test chamber 206.

At step 504, the valve 212b (referring to FIG. 2) may be actuated from a closed position to an open position to allow for pressure equalization within the test chamber 206. The piston 208 (referring to FIG. 2) may translate from a first position to a second position within the test chamber 206. Once the piston 208 is at the second position, the method 500 may proceed to step 506. In one or more embodiments, step 504 may not be limited to usage of the piston 208. Any suitable components and/or operations may be used in place of the piston 208, such as a vane pump, a peristaltic pump, air pressure, squeeze bulb, and the like.

At step 506, the heat source 210 (referring to FIG. 2) may increase the temperature within the test chamber 206 to produce vapors from the sample of the portion of the flow of fluid 216. The vapors from the sample of the portion of the flow of fluid 216 may flow up and out of the test chamber 206 through the secondary conduit 220 (referring to FIG. 2) as the valve 212b is open to provide for a pressure gradient. As the vapors from the sample of the portion of the flow of fluid 216 flow through the secondary conduit 220, the vapors may interact with the chemical sensor array 214 (referring to FIG. 2), wherein the chemical sensor array 214 is disposed along the secondary conduit 220.

At step 508, the chemical sensor array 214 may determine a composition of the vapors from the sample of the portion of the flow of fluid 216. The one or more chemical sensors 222 (referring to FIG. 2) may be operable to measure a change in electrical resistance based, at least in part, on one or more gas particles of the vapors interacting with each of the one or more chemical sensors 222. The measurements of the change in electrical resistance may be used to determine which compounds are present within the vapors from the sample of the portion of the flow of fluid 216 and at what quantity. In one or more embodiments, the information handling system 128 (referring to FIG. 1) may be operable to process, analyze, display, and any combinations thereof the measurements from the chemical sensor array 214. Further, the information handling system 128 may be configured to transmit instructions to any one of the components of the chemical sensor system 126 in order to operate.

At step 510, the chemical sensor array 214 may terminate operating to obtain measurements of the vapors from the sample of the portion of the flow of fluid 216. The valve 204b may be actuated to an open position to provide for pressure equalization for the piston 208. The piston 208 may be actuated to translate back to the first position. As the piston 208 translates, any remaining vapors or sample of fluid 216 may be directed to flow through the diverting conduit 202 and return to the main flow of fluid 216. Afterwards, the valve 212a may be actuated to an open position to start a purging cycle.

At step 512, a flow of a secondary fluid may be introduced through the secondary conduit 220 to clean the test chamber 206, the chemical sensor array 214, the secondary conduit 220, and combinations thereof. Once cleaning the aforementioned components has completed, the second set of valves 212a,b may be actuated to a closed position, and the valve 204a may be actuated to an open position to allow for a separate sample of the flow of fluid 216 diverted from the main flow of fluid 216 to be collected in the test chamber 206. The method 500 proceeds to end and may be repeated any suitable number of times.

An embodiment of the present disclosure is a method for determining a composition of a fluid, comprising diverting a sample of a portion of the fluid to a test chamber; actuating a heat source disposed around the test chamber to increase the temperature within the test chamber to produce vapors from the sample of the portion of the fluid; directing the vapors from the sample of the portion of the fluid to a chemical sensor array comprising one or more chemical sensors; and determining a composition of the vapors from the sample of portion of the fluid, wherein the composition of the vapors is associated with the composition of the fluid.

In one or more embodiments described in the preceding paragraph, further comprising actuating a first set of valves disposed along a diverting conduit to provide the sample of the portion of the fluid to flow into the test chamber. In one or more embodiments described above, wherein the diverting conduit is disposed in parallel to a main conduit configured to facilitate a main flow of the fluid. In one or more embodiments described above, further comprising: transmitting the composition of the vapors to an information handling system; and determining a wellbore operation based, at least in part, on the determined composition of the vapors. In one or more embodiments described above, further comprising actuating a second set of valves disposed along a secondary conduit to provide for the flow of a secondary fluid during a purging cycle. In one or more embodiments described above, wherein the secondary conduit is fluidly coupled to the test chamber and the chemical sensor array. In one or more embodiments described above, further comprising: directing a flow of a secondary fluid to clean the test chamber and the chemical sensor array during the purging cycle. In one or more embodiments described above, further comprising actuating the one or more chemical sensors to measure a change in electrical resistance based, at least in part, on one or more gas particles of the vapors interacting with each of the one or more chemical sensors.

Another embodiment of the present disclosure is a non-transitory computer-readable medium comprising instructions that are configured, when executed by a processor, to: divert a sample of a portion of the fluid to a test chamber; actuate a heat source disposed around the test chamber to increase the temperature within the test chamber to produce vapors from the sample of the portion of the fluid; direct the vapors from the sample of the portion of the fluid to a chemical sensor array comprising one or more chemical sensors; and determine a composition of the vapors from the sample of portion of the fluid, wherein the composition of the vapors is associated with the composition of the fluid.

In one or more embodiments described in the preceding paragraph, wherein the instructions are further configured to: actuate a first set of valves disposed along a diverting conduit to provide the sample of the portion of the fluid to flow into the test chamber. In one or more embodiments described above, wherein the instructions are further configured to: transmit the composition of the vapors to an information handling system; and determine a wellbore operation based, at least in part, on the determined composition of the vapors. In one or more embodiments described above, wherein the instructions are further configured to: actuate a second set of valves disposed along a secondary conduit to provide for the flow of a secondary fluid during a purging cycle. In one or more embodiments described above, wherein the instructions are further configured to: direct a flow of a secondary fluid to clean the test chamber and the chemical sensor array during the purging cycle. In one or more embodiments described above, wherein the instructions are further configured to: actuate the one or more chemical sensors to measure a change in electrical resistance based, at least in part, on one or more gas particles of the vapors interacting with each of the one or more chemical sensors.

A further embodiment of the present disclosure is a chemical sensor system, comprising: a chemical sensor array, comprising one or more chemical sensors, wherein each of the one or more chemical sensors is operable to determine at least one individual type of compound within a vapor; a test chamber operable to receive a sample of a portion of a fluid; and a heat source disposed around the test chamber operable to increase the temperature within the test chamber to produce vapors from the sample of the portion of the fluid, wherein the vapors are directed to flow downstream to be analyzed by the chemical sensor array.

In one or more embodiments described in the preceding paragraph, further comprising a first set of valves disposed on a diverting conduit, wherein the test chamber is disposed between each one of the first set of valves. In one or more embodiments described above, wherein the diverting conduit is disposed in parallel to a main conduit configured to divert the portion of a flow of the fluid, wherein the main conduit is configured to facilitate a main flow of the fluid. In one or more embodiments described above, further comprising a second set of valves disposed on a secondary conduit, wherein the test chamber is disposed between each one of the second set of valves. In one or more embodiments described above, wherein the secondary conduit is disposed vertically above the diverting conduit and operable to facilitate the flow of a secondary fluid during a purging cycle. In one or more embodiments described above, further comprising an information handling system communicatively coupled to the chemical sensor array and operable to provide instructions to the chemical sensor array, the test chamber, and the heat source.

Unless indicated to the contrary, the numerical parameters set forth in the specification and attached claims are approximations that may vary depending upon the desired properties sought to be obtained by the embodiments of the present disclosure. At the very least, and not as an attempt to limit the application of the doctrine of equivalents to the scope of the claim, each numerical parameter should at least be construed in light of the number of reported significant digits and by applying ordinary rounding techniques.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The disclosure illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

What is claimed is:

1. A method for measurement of the composition of a fluid, comprising:
   diverting a sample of a portion of the fluid from a main conduit into a diverting conduit through a first set of valves with a test chamber disposed between the first set of valves, wherein the test chamber comprises a piston disposed vertically above a central axis of the diverting conduit, a heat source disposed around the test chamber, and one or more electro-chemical resistor sensors, wherein the piston is in a first position;
   actuating the first set of valves to close after the test chamber receives the sample of the portion of the fluid while the piston is in the first position;
   moving the piston to a second position;
   actuating the heat source to increase the temperature within the test chamber to produce vapors from the sample of the portion of the fluid after the piston is in the second position;
   directing the vapors from the sample of the portion of the fluid to the one or more electro-chemical resistor sensor; and
   determining a composition of the vapors from the sample of portion of the fluid, wherein the composition of the vapors is associated with the composition of the fluid.

2. The method of claim 1, further comprising actuating the one or more chemical sensors to measure a change in electrical resistance based, at least in part, on one or more gas particles of the vapors interacting with each of the one or more electro-chemical sensors.

3. The method of claim 1, further comprising:
   transmitting the composition of the vapors to an information handling system; and
   determining a wellbore operation based, at least in part, on the determined composition of the vapors.

4. The method of claim 1, further comprising actuating the first set of valves disposed along the diverting conduit to provide the sample of the portion of the fluid to flow into the test chamber.

5. The method of claim 4, wherein the diverting conduit is disposed in parallel to the main conduit.

6. The method of claim 1, further comprising actuating a second set of valves disposed along a secondary conduit disposed parallel to and vertically above the diverting conduit to provide for a flow of a secondary fluid during a purging cycle.

7. The method of claim 6, wherein the secondary conduit is fluidly coupled to the test chamber and the one or more electro-chemical sensors.

8. The method of claim 6, further comprising:
   directing the flow of the secondary fluid to clean the test chamber and the one or more electro-chemical sensors during the purging cycle.

9. A non-transitory computer-readable medium comprising instructions that are configured, when executed by a processor, to:
   divert a sample of a portion of the fluid from a main conduit into a diverting conduit through a first set of valves with a test chamber disposed between the first set of valves, wherein the test chamber comprises a piston disposed vertically above a central axis of the diverting conduit, a heat source disposed around the test chamber, and one or more electro-chemical resistor sensors, wherein the piston is in a first position;
   actuate the first set of valves to close after the test chamber receives the sample of the portion of the fluid while the piston is in the first position;

moving the piston to a second position;

actuate the heat source to increase the temperature within the test chamber to produce vapors from the sample of the portion of the fluid after the piston is in the second position;

direct the vapors from the sample of the portion of the fluid to the one or more electro-chemical sensors; and determine a composition of the vapors from the sample of portion of the fluid, wherein the composition of the vapors is associated with the composition of the fluid.

10. The non-transitory computer-readable medium of claim 9, wherein the instructions are further configured to:

actuate the first set of valves disposed along the diverting conduit to provide the sample of the portion of the fluid to flow into the test chamber.

11. The non-transitory computer-readable medium of claim 9, wherein the instructions are further configured to:

transmit the composition of the vapors to an information handling system; and determine a wellbore operation based, at least in part, on the determined composition of the vapors.

12. The non-transitory computer-readable medium of claim 9, wherein the instructions are further configured to:

actuate the one or more electro-chemical sensors to measure a change in electrical resistance based, at least in part, on one or more gas particles of the vapors interacting with each of the one or more electro-chemical sensors.

13. The non-transitory computer-readable medium of claim 9, wherein the instructions are further configured to:

actuate a second set of valves disposed along a secondary conduit disposed parallel to and vertically above the diverting conduit to provide for a flow of a secondary fluid during a purging cycle, wherein the secondary conduit is fluidly coupled to the test chamber and the one or more electro-chemical sensors.

14. The non-transitory computer-readable medium of claim 13, wherein the instructions are further configured to:

direct the flow of the secondary fluid to clean the test chamber and the chemical sensor array during the purging cycle.

15. A method for measurement of the composition of a fluid, comprising:

actuating a first set of valves to an open position;

diverting a sample of a portion of the fluid from a main conduit into a diverting conduit in a chemical sensor system, wherein the chemical sensor system comprises the first set of valves, a piston disposed vertically above a central axis of the diverting conduit, a heat source disposed around a test chamber, one or more electro-chemical resistor sensors, a secondary conduit disposed vertically above the diverting conduit and operable to facilitate a flow of a secondary fluid during a purging cycle controlled by a second set of valves in a closed position before measurement, wherein the piston is in a first position;

actuating the first set of valves to a closed position;

moving the piston to a second position;

actuating the heat source to increase the temperature within the test chamber to produce vapors from the sample of the portion of the fluid;

opening one of the valves of the second set of valves located after the one or more electro-chemical sensors;

directing the vapors from the sample of the portion of the fluid to a chemical sensor array comprising one or more electro-chemical sensors;

determining a composition of the vapors from the sample of portion of the fluid, wherein the composition of the vapors is associated with the composition of the fluid;

opening one of the valves of the first set of valves located after the piston;

moving the piston to the first position;

opening the second valve of the second set of valves located before the piston; and closing the second set of valves.

* * * * *